US012734168B2

(12) United States Patent
Bianco et al.

(10) Patent No.: US 12,734,168 B2
(45) Date of Patent: Sep. 15, 2026

(54) DELTA OPIOID RECEPTOR ANTAGONISTS REPROGRAM IMMUNOSUPPRESSIVE MICROENVIRONMENT TO BOOST IMMUNOTHERAPY

(71) Applicant: H. LEE MOFFITT CANCER CENTER AND RESEARCH INSTITUTE, INC., Tampa, FL (US)

(72) Inventors: James Bianco, Seattle, WA (US); Paulo Rodriguez, Tampa, FL (US)

(73) Assignee: H LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 808 days.

(21) Appl. No.: 17/912,300

(22) PCT Filed: Mar. 16, 2021

(86) PCT No.: PCT/US2021/022464
§ 371 (c)(1),
(2) Date: Sep. 16, 2022

(87) PCT Pub. No.: WO2021/188473
PCT Pub. Date: Sep. 23, 2021

(65) Prior Publication Data

US 2023/0158016 A1 May 25, 2023

Related U.S. Application Data

(60) Provisional application No. 63/002,292, filed on Mar. 30, 2020, provisional application No. 62/990,364, filed on Mar. 16, 2020.

(51) Int. Cl.
*A61K 31/485* (2006.01)
*A61P 35/00* (2006.01)

(52) U.S. Cl.
CPC ........... *A61K 31/485* (2013.01); *A61P 35/00* (2018.01)

(58) Field of Classification Search
CPC .. A61K 31/485; A61K 39/39; A61K 39/0008; A61K 31/7105; A61K 45/06; A61K 38/08; A61K 38/07; A61P 25/00; A61P 35/00
USPC .......................................................... 514/282
See application file for complete search history.

(56) References Cited

U.S. PATENT DOCUMENTS

2016/0339099 A1 11/2016 Wood
2017/0202902 A1 7/2017 Mclaughlin et al.
2018/0280435 A1* 10/2018 Fisher et al.
2018/0298100 A1 10/2018 Wigginton et al.
2019/0321357 A1 10/2019 Griffin et al.

FOREIGN PATENT DOCUMENTS

WO WO 2007/131154 * 11/2007
WO WO-2007131154 A2 * 11/2007 .............. A61P 37/04
WO WO-2018022666 A1 * 2/2018 ......... A61K 38/2271
WO 2019186207 A1 10/2019

OTHER PUBLICATIONS

House et al., "Suppression Of Immune Function By Non-Peptidic Delta Opioid Receptor Antagonists", Neuroscience Letters 198 (1995) 119-122. (Year: 1995).*
International search report and written opinion in PCT/US2021/022464. Mailed Jul. 12, 2021. 15 pages.
Jamali et al. "A novel adjuvant, the general oploid antagonist naloxone, elictis a robust cellular immune response for a DNA vaccine." International Immunology, Jan. 27, 2009.
Aboalsoud et al. "The effect of low-dose naltrexone on solid Ehrlich carcinoma in mice: The role of OGFr, BCL2, and Immune response." International Immunology. Dec. 10, 2019.

* cited by examiner

*Primary Examiner* — Kortney L. Klinkel
*Assistant Examiner* — Grace Ching Hsu
(74) *Attorney, Agent, or Firm* — Mintz, Levin, Cohn, Ferris, Glovsky and Popeo, P.C.

(57) ABSTRACT

Disclosed are compositions and methods for mediating immunosuppressive myelopoiesis. Additionally, disclosed herein are combination therapies for treating cancers and methods of using the same.

5 Claims, 3 Drawing Sheets

All the experiments were done in triplicate

Naltriben mesylate (NTB) $IC_{50}$ 46.1 µM

Naltrindole hydrochloride (NTD) $IC_{50}$ 68.06 µM

DELTA OPIOID RECEPTOR ANTAGONISTS REPROGRAM IMMUNOSUPPRESSIVE MICROENVIRONMENT TO BOOST IMMUNOTHERAPY

I. STATEMENT OF GOVERNMENT SUPPORT

This invention was made with government support under Grant No. CA184185 awarded by National Institutes of Health. The government has certain rights in the invention.

I. BACKGROUND

The tumor microenvironment is defined on a range of non-inflamed (tumorigenic) to inflamed (immunogenic) tumors Inflamed tumors are characterized by marked infiltration of immune effector cells indicating a pre-existing and ongoing immune response. They also have high tumor mutational burden leading to high tumor antigen burden facilitating cytotoxic T cell activation. In addition, immune potentiating chemokine expression like Th1 cytokines notably IL-2, IFNγ allows immune cell infiltration. Checkpoint inhibitors like anti-PD-1, or PD-L1, CTLA 4, or T cell activators (OX40, CD 137) are most effective in inflamed tumors Non-inflamed tumors are the predominant tumor phenotype and, unlike inflamed tumors, are characterized by poor immune cell infiltration, lack of cytotoxic effector activated T-cells, impaired ability to present tumor antigen. They also lack expression of chemo-attractants, poor immune cell infiltration. Primary chemokine expression, are notably Th2 immune suppressing cytokines like TGFβ, IL-10

The microenvironment is composed of a variety of cellular components such as tumor associated fibroblasts or Myeloid Derived Suppressor Cells (MDSCs). MDSCs are types of cells produced in the bone marrow and are normally only present during pregnancy and are believed to be responsible for maternal-fetal tolerance. However, in the development of cancer, MDSCs begin to be abnormally produced and circulate to tissues and organs in the body. MDSCs are the primary cellular component of microenvironment which promotes a permissive immune environment necessary for growth of malignant cells. MDSCs can exert suppressive effects on multiple immune cell types, including T cells and NK cells. Functionally distinct from neutrophils and monocytes, MDSCs suppress immune cell activity using a number of pathways, including the upregulation of arginase-1 (Arg1). This leads to arginine starvation and the upregulation of reactive oxygen species (ROS), such as the inducible nitric oxide synthase (iNOS) among other factors (Cox2, PGE2, IDO, IL-10, IL-6, TGF-β)

Recent research has demonstrated that circulating levels of MDSCs predict resistance to and hinder the anti-tumor activity of checkpoint inhibitors, immune cell activators and cellular therapies (NK cells, CTL's) Immune effectors like checkpoint inhibitors have revolutionized the treatment of cancer demonstrating impressive antitumor activity and, in some settings, improving survival. The impact checkpoint inhibitors has had on both the scientific and clinical communities was underscored by the Researcher's original research identifying checkpoints proteins (PD-1, PD-L1, CTLA-4) being awarded the 2018 Nobel Prize in Medicine. Unfortunately, checkpoint inhibitors work in just a minority of patients. Only patients with high circulating or tumor expression of checkpoint proteins will respond. This "shedding" of checkpoint proteins by tumors is, in part, the result of inflammation being present at the time checkpoint inhibitors are administered. As such, checkpoint inhibitors work in patients whose tumors are inflamed.

Checkpoint inhibitors are less effective or ineffective in patients with low or no circulating levels or tumor expression of checkpoint proteins denoting tumors than are non-inflamed. Converting tumors from non-inflamed (tumorigenic) to inflamed (immunogenic) would represent a major advance in immune therapy expanding the use of immune effectors like checkpoint inhibitors to a larger proportion of patients across a wider variety of tumor types.

Myeloid-derived suppressor cells (MDSCs) also represent an important class of immunoregulatory cells that can be activated to suppress T cell and other immune cell types functions. These MDSCs can inhibit T cell functions through cell surface interactions and the release of soluble mediators. MDSCs accumulate in the inflamed tissues and lymphoid organs of patients with autoimmune diseases. Much of our knowledge of MDSC function has come from studies involving cancer models, however many recent studies have helped to characterize MDSC involvement in autoimmune diseases. MDSCs are a heterogeneous group of immature myeloid cells with a number of different functions for the suppression of T cell responses. However, we have yet to fully understand their contributions to the development and regulation of autoimmune diseases. A number of studies have described beneficial functions of MDSCs during autoimmune diseases, and thus there appears to be a potential role for MDSCs in the treatment of these diseases.

MDSCs are accumulated in the inflammatory sites during some autoimmune disorders, such as rheumatoid arthritis (RA) and can be an important factor in the pathogenesis of these diseases. Some research has shown the anti-inflammatory role of MDSCs during the RA progression and supports the hypothesis that MDSCs can be a potential treatment option for autoimmunity with their immunosuppressive activity.

II. SUMMARY

Disclosed are delta opioid receptor (DOR) antagonist and agonists and methods of their use in immunotherapy.

In one aspect, disclosed herein are methods of reprogramming an immunosuppressive microenvironment of a tumor in a subject comprising administering to the subject a DOR antagonist (such as, for example, Dmt-Tic, naltriben mesylate (NTB), naltrindole hydrochloride (NTD), benzofuran analog of naltrindole, (+/−)-4-((alpha-R*)-alpha-((2S*,5R*) Allyl-2,5-dimethyl-1-piperazinyl)-3-hydroxybenzyl)-N,N-diethylbenzamide, and 7-benyllidenenaltrexone as well as any other DOR antagonist disclosed herein, including, but not limited to conjugated versions of any the DOR antagonists disclosed herein).

Also disclosed herein are methods of reprogramming myeloid-derived suppressor cells (MDSC) in a tumor in a subject into immunostimulatory myeloid cells comprising administering to the subject a DOR antagonist. In one aspect, the reprogramming of the MDSC can be a modulation of the proliferation of MDSCs.

In one aspect disclosed herein are methods of increasing the efficacy of an adoptive immunotherapy (such as, for example, administration of chimeric antigen receptor (CAR) T cells, CAR NK cells, tumor infiltrating lymphocytes (TILs), tumor infiltrating NK cells (TINKs), and/or marrow infiltrating lymphocytes (MILs)) said method comprising administering to the subject a DOR antagonist; wherein the administration of the DOR antagonist reprograms immunosuppressive microenvironment in a tumor thereby boosting the efficacy of the adoptive immunotherapy.

Also disclosed herein are methods of increasing the efficacy of an adoptive immunotherapy said method comprising a) obtaining a donor population of cells for immunotherapy (such as, for example, administration of chimeric antigen receptor (CAR) T cells, CAR NK cells, tumor infiltrating lymphocytes (TILs), tumor infiltrating NK cells (TINKs), and/or marrow infiltrating lymphocytes (MILs) from an autologous, haplo-identical, or allogeneic donor source); and b) contacting said cells with a DOR antagonist; wherein the administration of the DOR antagonist reprograms the susceptibility of the donor cells to immunosuppressive myelopoiesis thereby boosting the efficacy of the adoptive immunotherapy. In one aspect, the donor population of cells are contacted with the increasing the efficacy of an adoptive immunotherapy ex vivo.

Also disclosed herein are methods of stimulating endogenous T cells (such as, for example TILs or MILs,) NK cells (such as, for example TINKs) and/or NK T cells in a subject to kill a tumor comprising administering to a subject a DOR antagonist wherein the administration of the DOR antagonist reduces or reduces the effects of one or more immunosuppressive elements in the tumor.

In one aspect, disclosed herein are methods of reprogramming an immunosuppressive myelopoiesis in a tumor of any preceding aspect, methods of reprogramming myeloid-derived suppressor cells (MDSC) in a tumor of any preceding aspect, methods of increasing the efficacy of an adoptive immunotherapy, oncolytic viral therapy of any preceding aspect, and/or methods of stimulating endogenous T cells or other cytotoxic immune cell subsets (M1 macrophages etc) in a subject to kill a tumor of any preceding aspect, wherein the DOR antagonist comprises a RNAi, CRISPR, anti-sense oligonucleotides, small molecule (such as, for example, Dmt-Tic, naltriben mesylate (NTB), naltrindole hydrochloride (NTD), benzofuran analog of naltrindole, (+/−)-4-((alpha-R*)-alpha-((2S*,5R*)-4-Allyl-2,5-dimethyl-1-piperazinyl)-3-hydroxybenzyl)-N,N-diethylbenzamide, and 7-benyllidenenaltrexone as well as any other DOR antagonist disclosed herein, including, but not limited to conjugated versions of any the DOR antagonists disclosed herein), peptide, protein, or antibody. In some aspect, the DOR antagonist comprises DmtTic conjugated IgG (isotype) antibody. In one aspect, Also disclosed herein are combination immunotherapies comprising an adoptive immunotherapy (such as, for example, administration of chimeric antigen receptor (CAR) T cells, CAR NK cells, tumor infiltrating lymphocytes (TILs), TINKs and/or marrow infiltrating lymphocytes (MILs)) and a DOR antagonist like DmtTic conjugated IgG (isotype) antibody.

In one aspect, disclosed herein are methods of treating, inhibiting, reducing, ameliorating, and/or preventing a cancer and or metastasis in a subject comprising administering to a subject the combination therapy of any preceding aspect. For example, disclosed herein are methods of treating, inhibiting, reducing, ameliorating, and/or preventing a cancer and or metastasis in a subject comprising administering to a subject an (such as, for example, administration of chimeric antigen receptor (CAR) T cells, CAR NK cells, tumor infiltrating lymphocytes (TILs), tumor infiltrating NK cells (TINKs), and/or marrow infiltrating lymphocytes (MILs)) and DOR antagonist (including, but not limited to RNAi, anti-sense oligo's small molecules (such as, for example, Dmt-Tic, naltriben mesylate (NTB), naltrindole hydrochloride (NTD), benzofuran analog of naltrindole, (+/−)-4-((alpha-R*)-alpha-((2S*,5R*)-4-Allyl-2,5-dimethyl-1-piperazinyl)-3-hydroxybenzyl)-N,N-diethylbenzamide, and 7-benyllidenenaltrexone as well as any other DOR antagonist disclosed herein, including, but not limited to conjugated versions of any the DOR antagonists disclosed herein). In one aspect, the CAR T cells, CAR NK cells, TILs, TINKs, and/or MILs can be obtained from a donor source including, but not limited to autologous, haplo-identical, or allogeneic donors. I Also disclosed herein are methods of treating, inhibiting, reducing, ameliorating, and/or preventing a cancer and or metastasis of any preceding aspect, wherein the CAR T cells, CAR NK cells, TILs, TINKs, and/or MILs that comprise the adoptive immunotherapy are contacted with the DOR antagonist ex vivo prior to administration to the subject.

Also disclosed herein are methods of treating, inhibiting, reducing, ameliorating, and/or preventing a cancer and or metastasis of any preceding aspect, wherein the CAR T cells, CAR NK cells, TILs, TINKs, and/or MILs that comprise the adoptive immunotherapy are contacted with the DOR antagonist in vivo.

In some aspect, methods of treating, inhibiting, reducing, decreasing, ameliorating and/or preventing an autoimmune disease in a subject comprising administering to the subject a DOR agonist and methods of treating, inhibiting, reducing, decreasing, ameliorating and/or preventing the symptoms associated with a microbial infection in a subject comprising administering to the subject a DOR agonist. In some aspects, the methods can further comprise the administration of an immunosuppressor.

These results indicate that selective agonists and antagonists bind differently to the delta receptor and show that Asp-95 contributes to high affinity delta-selective agonist binding. The identification of a key residue involved in selective agonist binding to the delta opioid receptor will facilitate the development of novel therapeutic reagents that can be used for the treatment of chronic pain and other conditions.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows elevated expression of DOR in tumor-MDSC correlates with a superior capacity to impair T cell proliferation. Bars are mean of T cell proliferation ±SEM by flow cytometry after 72 hours of co-culture. N=3

IV. DETAILED DESCRIPTION

Figure 1:
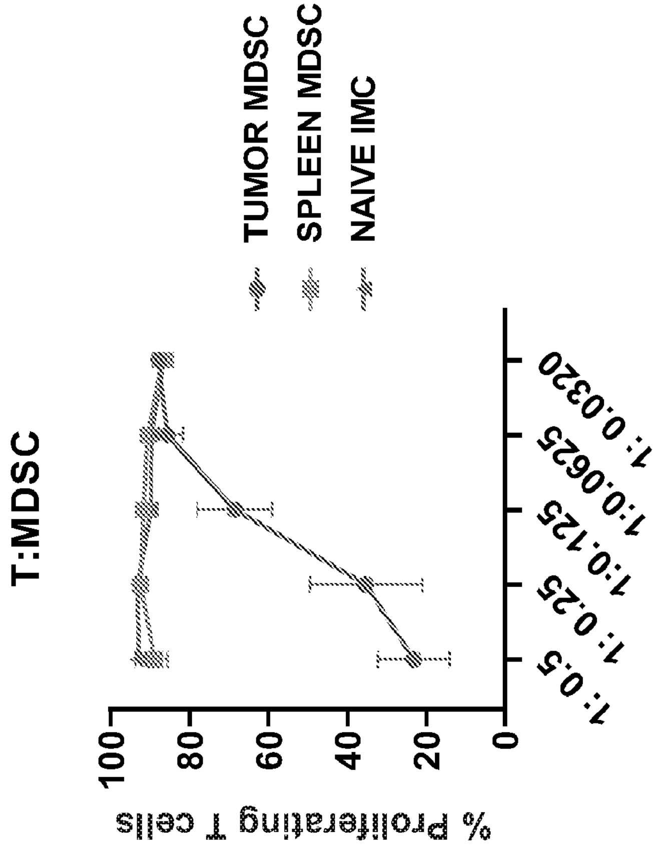
Figure 1:
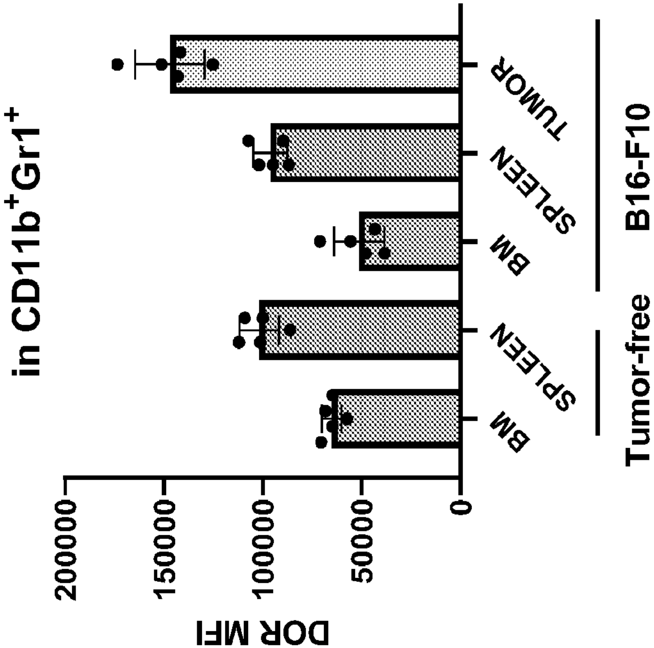
Figure 2:
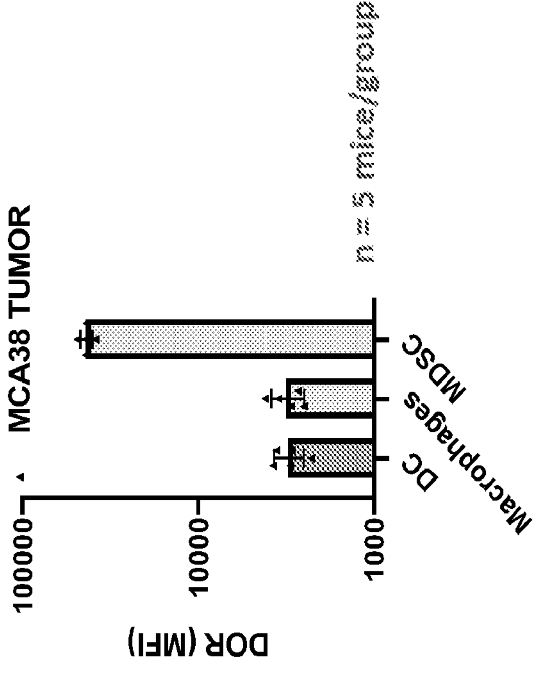
FIG. 2 shows tumor-MDSC display higher expression of DOR compared to other tumor-associated myeloid subsets.
Figure 2:
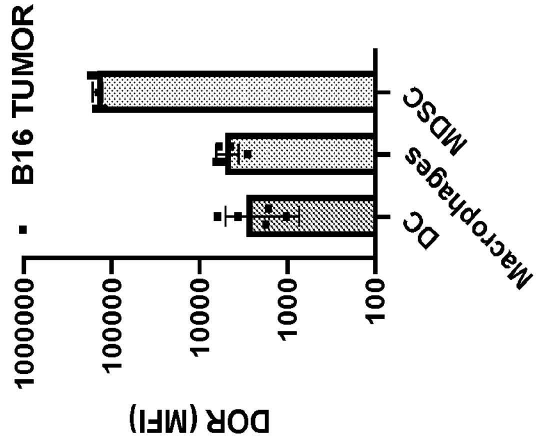
Figure 2:
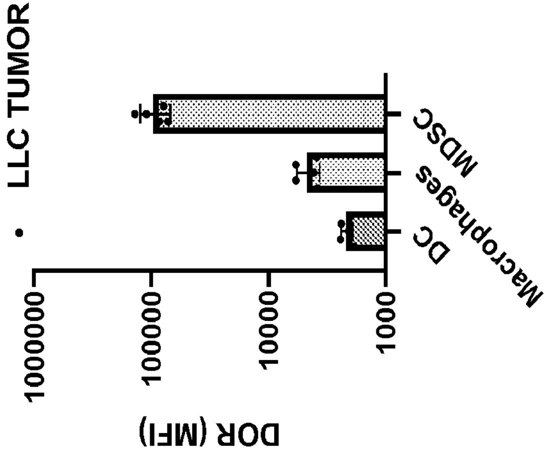
Figure 3:
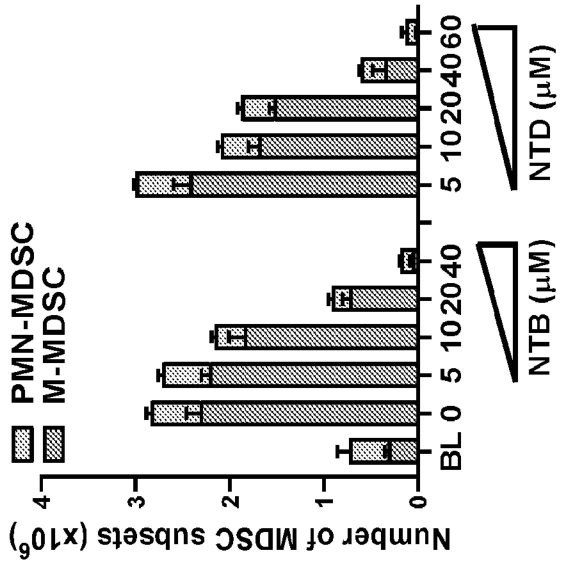
FIG. 3 shows that DOR antagonists prevent the development of M-MDSC from bone marrow precursors. Figure shows flow cytometry (using DAPI, left), the absolute number of generated MDSC ($CD11b^+Gr1^+$) (center), and the number of MDSC substets M-MDSC ($CD11b^+ Ly6G^{neg}Ly6C^{high}$) and PMN-MDSC ($CD11b^+Ly6G^+ Ly6C^{low}$) (right).
Figure 3:
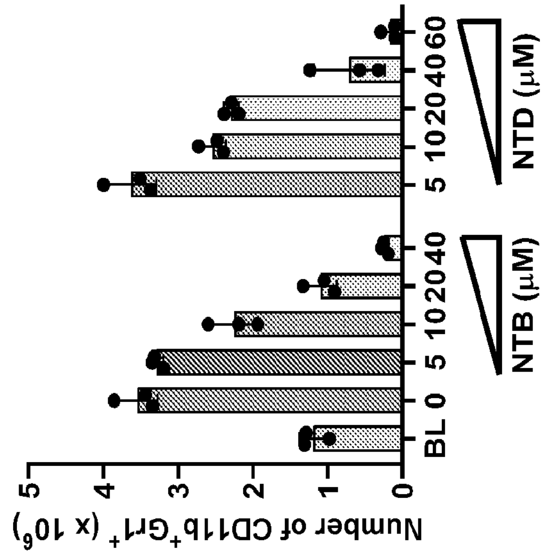
Figure 3:
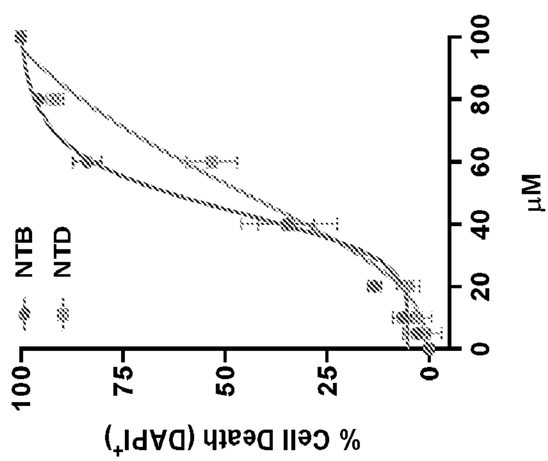

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, pallatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods of Use of DOR Antagonists and Combination Therapies Including DOR Antagonists MDSCs role in promoting a permissive, immunosuppressed environment for tumors to live and grow while escaping immune recognition and attack has garnered the attention of the scientific community as it represents a novel target with potential to alter the tumorigenic immunosuppressive microenvironment to a more immunogenic environment.

Given the central role MDSCs play in providing an environment for tumors to grow and evade immune attack there have been a number of approaches looking to modulate their effects on the microenvironment: 1) inhibition of proliferation and migration to reduce their numbers in the tumor microenvironment; 2) controlling the MDSC population by targeting their differentiation into mature cells such as dendritic cells and stimulatory macrophages; and 3) inhibiting MDSC functionality.

This is the most investigated approach targeting PGE2, or COX2 with inhibitors to decrease production of Arginase or reactive oxygen species through inducible nitric oxide synthetase. To date there has not been a single MDSC target that controls multiple pathways associated with their immunosuppressive capacity.

The Delta Opioid Receptor (DOR) is a G-protein coupled tyrosine kinase which has been reported to be expressed on a variety of tumors like NSCLC, Breast, Colon cancer. Receptor activation is intimately involved in gene expression associated with a tumor's malignant phenotype including invasion and metastasis. The receptor is also been reported to be expressed on a variety of immune cells mainly T cells, and NK cells. There are mixed reports on the effects of receptor activation on the immune system. Expression of the DOR on MDSCs has not previously been reported. We examined the expression of the DOR in tumor, splenic. BM-MDSCs and in vitro BM precursors. Receptor inhibition markedly reduced production of MDSC immunosuppressive factors iNOS, Arg-1, Cox2 supporting the hypothesis that the DOR represents a new, previously unreported target for modulating MDSC function and its associated immunosuppressive impact on the tumor microenvironment and autoimmune conditions.

In one aspect, disclosed herein are methods of reprogramming an immunosuppressive myelopoiesis in a tumor in a subject comprising administering to the subject a DOR antagonist (such as, for example, Dmt-Tic, naltriben mesylate (NTB), naltrindole hydrochloride (NTD), benzofuran analog of naltrindole, (+/−)-4-((alpha-R*)-alpha-((2S*,5R*) Allyl-2,5-dimethyl-1-piperazinyl)-3-hydroxybenzyl)-N,N-diethylbenzamide, and 7-benyllidenenaltrexone as well as any other DOR antagonist disclosed herein, including, but not limited to conjugated versions of any the DOR antagonists disclosed herein).

In one aspect, it is understood and herein contemplated that immunosuppressive myelopoiesis is mediated by myeloid-derived suppressor cells (MDSC) and these suppressor cells can be converted to immunostimulatory myeloid cells through the effect of DOR antagonist. Accordingly, disclosed herein are methods of reprogramming myeloid-derived suppressor cells (MDSC) in a tumor in a subject into immunostimulatory myeloid cells comprising administering to the subject a DOR antagonist.

The result of turning an immunosuppressive environment into an immunostimulatory environment can have a significant effect on the efficacy of immunotherapy. In one aspect disclosed herein are methods of increasing the efficacy of an adoptive immunotherapy (such as, for example, administration of chimeric antigen receptor (CAR) T cells, CAR NK cells, tumor infiltrating lymphocytes (TILs), tumor infiltrating NK cells (TINKs), and/or marrow infiltrating lymphocytes (MILs)) said method comprising administering to the subject a DOR antagonist; wherein the administration of the DOR antagonist reprograms immunosuppressive myelopoiesis in a tumor thereby boosting the efficacy of the adoptive immunotherapy. For example, disclosed herein are methods of increasing the efficacy of an adoptive immunotherapy said method comprising a) obtaining a donor population of cells for immunotherapy (such as, for example, administration of chimeric antigen receptor (CAR) T cells, CAR NK cells, tumor infiltrating lymphocytes (TILs), tumor infiltrating NK cells (TINKs), and/or marrow infiltrating lymphocytes (MILs) from an autologous, haploidentical, or allogeneic donor source); and b) contacting said cells with a DOR antagonist; wherein the administration of the DOR antagonist reprograms the susceptibility of the donor cells to immunosuppressive myelopoiesis thereby boosting the efficacy of the adoptive immunotherapy. In one aspect, the donor population of cells are contacted with the increasing the efficacy of an adoptive immunotherapy ex vivo.

The same immunostimulatory action of DOR antagonists can be used to stimulate endogenous immune responses. Thus, also disclosed herein are methods of stimulating endogenous T cells (such as, for example TILs or MILs) in a subject to kill a tumor comprising administering to a subject a DOR antagonist wherein the administration of the DOR antagonist reduces or reduces the effects of one or more immunosuppressive elements in the tumor.

As used herein the DOR antagonist can comprise a RNAi, small molecule, peptide, protein, or antibody. Examples of DOR antagonists that may be used in the methods disclosed herein include, but are not limited to, Dmt-Tic (e.g., DMT-Tic-OH or DMT-Tic-Ala-OH), naltrindole, naltriben, trazodone, naltriben mesylate (NTB) or naltrindole hydrochloride (NTD), buprenorphine, ICI 174,864 (N,N-diallyl-Tyr-Aib-Aib-Phe-Leu), N-Benzylnaltrindole, BNTX (7-Benzylidenenaltrexone), SoRI-9409, ICI 154,129 (N,N-Diallyl-Tyr-Gly-φ-($CH_2S$)-Phe-Leu-OH, (+/−)-4-((alpha-R*)-alpha-((2S*,5R*)-4-Allyl-2,5-dimethyl-1-piperazinyl)-3-hydroxybenzyl)-N,N-diethylbenzamide, or SDM25N (4bS,8R,8aS,14bR)-5,6,7,8,14,14b-Hexahydro-7-(2-methyl-2-propenyl)-4,8-methanobenzofuro[2,3-a]pyrido[4,3-b]carbazole-L8a(9H)-diol.

Dmt-Tic is represented by

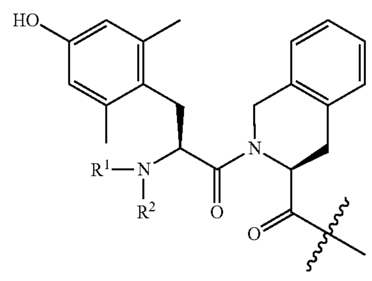

where $R^1$ and $R^2$ are independently selected from H and $CH_3$.

Specific examples of the Dmt-Tic moiety can be found in Balboni et al. Biorg Med Chem 2003, 11:5435-5441, which is incorporated by referenced herein in its entirety for examples of Dmt-Tic moieties. Dmt-Tic is described in U.S. Pat. Nos. 10,426,843 and 10,449,227, which are each incorporated herein by reference in its entirety. Other delta opioid receptor antagonists are described in U.S. Pat. No. 5,352,680 (Portoghese and Takemori), Portoghese P S et al., *J. Med. Chem.,* 1990, 33, 1714-1720, Mosberg H I et al., *Letters in Peptide Science,* 1994, (1(2):69-72, and Korlipara V L et al.,

*J. Med. Chem.*, 1994, 37, 1881-1885, which are each incorporated herein by reference in its entirety.

In some examples the DOR antagonist can be conjugated to an immune effector. Non-limiting examples of immune effector proteins include CD86, CD80, 41BBL, OX40, IL-15, Anti-Programmed Death-1 (PD1), anti-PD-L1, anti-B7-Hl, IL-12, Anti-CD40, CD40 ligand, IL-7, Anti-CD137 (anti-4-1BB), Anti-TGF-β, Anti-IL-10 Receptor or Anti-IL-10, FMS-like Tyrosine Kinase 3 Ligand (Flt3L), Anti-Glucocorticoid-Induced TNF Receptor (GITR), chemokine (C—C motif) ligand 21 (CCL21), Anti-OX40, Anti-B7-H4, Anti-Lymphocyte Activation Gene-3 (LAG-3), CD258 (also referred to as LIGHT or TNFSF14), or Anti-CTLA4. In some aspect, the immune effector can be a bispecific antibody or fragment thereof.

As noted throughout this application, it is understood and herein contemplated that the methods and DOR antagonists disclosed herein used alone or in combination with adoptive immunotherapies (such as, for example, CAR T cell, CAR NK cell, TIL, TINK, and/or MIL immunotherapies) can treat, inhibit, reduce, prevent, and/or ameliorate any disease where uncontrolled cellular proliferation occurs such as cancers (including, but not limited to primary cancers and metastasis). Accordingly, disclosed herein are combination immunotherapies comprising an adoptive immunotherapy (such as, for example, administration of chimeric antigen receptor (CAR) T cells, CAR NK cells, tumor infiltrating lymphocytes (TILs), tumor infiltrating NK cells (TINKs), and/or marrow infiltrating lymphocytes (MILs)) and a DOR antagonist.

In one aspect, disclosed herein are methods of treating, inhibiting, reducing, ameliorating, and/or preventing a cancer and or metastasis in a subject comprising administering to a subject the combination therapy of any preceding aspect. For example, disclosed herein are methods of treating, inhibiting, reducing, ameliorating, and/or preventing a cancer and or metastasis in a subject comprising administering to a subject an (such as, for example, administration of chimeric antigen receptor (CAR) T cells, CAR NK cells, tumor infiltrating lymphocytes (TILs), tumor infiltrating NK cells (TINKs), and/or marrow infiltrating lymphocytes (MILs)) and DOR antagonist (including, but not limited to RNAi, small molecules (such as, for example. Dmt-Tic, naltriben mesylate (NTB) or naltrindole hydrochloride (NTD), or any DOR antagonist disclosed herein), peptides, proteins, or antibodies). In one aspect, the CAR T cells, CAR NK cells, TILs, TINKs, and/or MILs can be obtained from a donor source including, but not limited to autologous, haploidentical, or allogeneic donors. Also disclosed herein are methods of treating, inhibiting, reducing, ameliorating, and/or preventing a cancer and or metastasis of any preceding aspect, wherein the CAR T cells, CAR NK cells, TILs, TINKs. And/or MILs that comprise the adoptive immunotherapy are contacted with the DOR antagonist ex vivo prior to administration to the subject. Also disclosed herein are methods of treating, inhibiting, reducing, ameliorating, and/or preventing a cancer and or metastasis of any preceding aspect, wherein the CAR T cells, CAR NK cells, TILs. TINKs, and/or MILs that comprise the adoptive immunotherapy are contacted with the DOR antagonist in vivo.

Further provided herein are methods of treating, inhibiting, reducing, ameliorating and/or preventing a disease, for example cancer in a subject, comprising administering to the subject an effective amount of a composition comprising an adoptive immunotherapy (such as, for example chimeric antigen receptor (CAR) T cell (CAR T cell) immunotherapy, Tumor infiltrating lymphocyte (TIL) immunotherapy, CAR NK cell immunotherapy, tumor infiltrating NK cells (TINKs), and or marrow infiltrating lymphocyte (MIL) immunotherapy) and any of the DOR antagonists disclosed herein.

Methods of killing a tumor cell are also provided herein. The methods comprise contacting a tumor cell with an effective amount of a DOR antagonist as disclosed herein and an adoptive immunotherapy. The methods can further include administering a second compound or composition (e.g., an anticancer agent) or administering an effective amount of ionizing radiation to the subject.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

In one aspect, it is understood and herein contemplated that successful treatment of a cancer in a subject is important and doing so may include the administration of additional treatments. Thus, the disclosed treatments can further include any anti-cancer therapy known in the art including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil-Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R—CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride). Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). In some instances in addition to the DOE antagonist, the treatment methods can further include the administration of checkpoint inhibitors including, but are not limited to antibodies that block PD-1 (such as, for example, Nivolumab (BMS-936558 or MDX1106), CT-011, MK-3475), PD-L1 (such as, for example, MDX-1105 (BMS-936559), MPDL3280A, or MSB0010718C), PD-L2 (such as, for example, rHIgM12B7), CTLA-4 (such as, for example, Ipilimumab (MDX-010), Tremelimumab (CP-675,206)), IDO, B7-H3 (such as, for example, MGA271, MGD009, omburtamab), B7-H4, B7-H3, T cell immunoreceptor with Ig and ITIM domains (TIGIT)(such as, for example BMS-986207, OMP-313M32, MK-7684, AB-154, ASP-8374, MTIG7192A, or PVSRIPO), CD96, -and T-lymphocyte attenuator (BTLA), V-domain Ig suppressor of T cell activation (VISTA)(such as, for example, JNJ-61610588, CA-170), TIM3 (such as, for example, TSR-022, MBG453, Sym023, INCAGN2390, LY3321367, BMS-986258, SHR-1702, R07121661), LAG-3 (such as, for example, BMS-986016, LAG525, MK-4280, REGN3767, TSR-033, BI754111, Sym022, FS118, MGD013, and Immutep) as well as antibodies that block the ligands that innervate PD-1, CTLA-4, LAG-3, TIGIT, CD96, BTLA, B7-H3, VISTA, and TIM-3 including, but not limited to antibodies that block PD-L1, fibrinogen-like protein 1 (FGL1), CD112, CD155, herpes virus entry mediator (HVEM), and Ceacam-1 from binding their respective receptors.

C. Methods of Use of DOR Agonists

As noted throughout this paper suppression of delta opioid receptors can decrease the immunosuppressive microenvironment of a tumor. Conversely innervating delta opioid receptors can increase the immunosuppressive microenvironment. In one aspect, it is understood and herein contemplated that by specifically targeting and activating the delta opioid receptor diseases that comprise an excessive or uncontrolled immune response (such as, for example, autoimmune diseases and microbial infections) can be treated or the symptoms resulting from the excessive or uncontrolled immune response can be reduced, inhibited, ameliorated, decreased, mitigated, and/or prevented. Accordingly, in one aspect, disclosed herein are methods of treating, inhibiting, reducing, decreasing, ameliorating, and/or preventing an autoimmune disease in a subject or the symptoms associated with the autoimmune disease or microbial infection comprising administering to the subject a DOR agonist. The DOR agonist may be a peptide or a non-peptide molecule. For example, as used herein, a non-limiting exemplary list of DOR agonist include, but are not limited to rubiscolin-6 and its derivatives, deltorphin and its derivatives, Leu-enkephalin, Met-enkephalin, DPDPE (D-Penicillamine (2, 5)-enkephalin) and its derivatives, DSLET, DADLE, biphalin, JOM-13, DTLET, DSTBULET, BUBU, BUBUC and non peptide agonists such as BU-48, BW373U86, C-8813, 7-spiroindanyloxymorphone (SIOM), N-phenethyl-14-ethoxymetopon, ADL-5859, SNC-40, SNC-80, SNC-86, SNC-162, DPI-221, DPI-287, DPI-3290, TAN-67, RWJ-394, 674, and norbuprenorphine. Other examples of DOR agonists can include any DOR agonist which are disclosed in U.S. Pat. No. 7,164,021, International PCT Application Publication NO. WO/2004060321, International PCT Application Publication NO. WO/22007116114, International PCT Application Publication NO. WO/2004026819, International PCT Application Publication NO. WO/1989000995, and European Patent Application No. 12305335.7, each of which is incorporated herein by reference in its entirety, As used herein, "autoimmune disease" refers to a set of diseases, disorders, or conditions resulting from an adaptive immune response (T cell and/or B cell response) against the host organism. In such conditions, either by way of mutation or other underlying cause, the host T cells and/or B cells and/or antibodies are no longer able to distinguish host cells from non-self-antigens and attack host cells baring an antigen for which they are specific. Examples of autoimmune diseases include, but are not limited to Achalasia, Acute disseminated encephalomyelitis, Acute motor axonal neuropathy, Addison's disease, Adiposis dolorosa, Adult Still's disease, Agammaglobulinemia, Alopecia areata, Alzheimer's disease, Amyloidosis, Ankylosing spondylitis, Anti-GBM/Anti-TBM nephritis, Antiphospholipid syndrome, Aplastic anemia, Autoimmune angioedema, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune myocarditis, Autoimmune oophoritis, Autoimmune orchitis, Autoimmune pancreatitis, Autoimmune polyendocrine syndrome, Autoimmune retinopathy, Autoimmune urticaria, Axonal & neuronal neuropathy (AMAN), Baló disease, Behcet's disease, Benign mucosal emphigoid, Bickerstaffs encephalitis, Bullous pemphigoid, Castleman disease (CD), Celiac disease, Chagas disease, Chronic fatigue syndrome, Chronic inflammatory demyelinating polyneuropathy (CIDP), Chronic recurrent multifocal osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes mellitus type 1, Discoid lupus, Dressler's syndrome, Endometriosis, Enthesitis, Eosinophilic esophagitis (EoE), Eosinophilic fasciitis, Erythema nodosum, Essential mixed cryoglobulinemia, Evans syndrome, Felty syndrome, Fibromyalgia, Fibrosing alveolitis. Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's encephalopathy, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Inflamatory Bowel Disease (IBD), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus nephritis, Lupus vasculitis, Lyme disease chronic. Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Ord's thyroiditis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schmidt syndrome, Schnitzler syndrome, Scleritis, Scleroderma, Sjögren's syndrome, Sperm & testicular autoimmunity, Stiff person syndrome (SPS), Subacute bacterial endocarditis (SBE), Susac's syndrome, Sydenham chorea, Sympathetic ophthalmia (SO), Systemic Lupus Erythematosus, Systemic scleroderma, Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Urticaria, Urticarial vasculitis, Uveitis, Vasculitis, Vitiligo, Vogt-Koyanagi-Harada Disease, and Wegener's granulomatosis (or Granulomatosis with Polyangiitis (GPA)).

In response to infection with a microbe such as, for example, a virus, bacterium, fungus, or parasite the host immune system attempts to eliminate the infecting microbe by employing arms of the innate and adaptive immune systems including the secretion of cytokines, antibodies, and effector mechanisms of granulocyte, monocyte, macrophage, dendritic cell, innate lymphoid cell, NK cells, NK T cells, T cells, B cells, and plasma cells. The innate and adaptive immune response to infecting pathogen (disease-causing microorganism) can include the burst in production of cytokines, chemokines, and proteolytic enzymes by granulocytes, monocytes, macrophages, dendritic cells, mast cells, innate lymphoid cells, T cells, B cells, NK cells, and NK T cells. Microbial inflammation can be localized to a specific organ- or can be systemic. Microbial inflammation can proceed in stages from acute to subacute and chronic with attendant tissue destruction and subsequent fibrosis. Left unchecked, the acute microbial inflammation can lead to sepsis and septic shock, the end stage of microbial inflammation. While the symptoms of some microbial infections result from the immunoregulatory effects or lytic actions of the infecting microbe, it is also understood that symptoms associated with many microbial infections are not the result of the infecting microbe, but the immune response to the infections. The disclosed methods are designed to address symptoms resulting from either situation.

"Pathogen" is an agent that causes infection or disease, especially a virus, bacterium, fungus, protozoa, or parsite.

It is understood that the pathogen can be a virus. Thus in one embodiment the pathogen can be selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2. In some embodiments, the coronavirus is SARS-CoV-2 or 2019-nCoV.

Also disclosed are methods wherein the pathogen is a bacterium. The pathogen can be selected from the group of bacteria consisting of *Mycobaterium tuberculosis, Mycobaterium bovis, Mycobaterium bovis* strain BCG, BCG substrains, *Mycobaterium avium, Mycobaterium intracellular, Mycobaterium africanum, Mycobaterium* kansasii, *Mycobaterium* marinum, *Mycobaterium* ulcerans, *Mycobaterium avium* subspecies paratuberculosis, *Nocardia asteroides*, other *Nocardia* species, *Legionella pneumophila*, other *Legionella* species, *Acetinobacter baumanii, Salmonella typhi, Salmonella enterica*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii* other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial species, Ehrlichia species, Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species, and *Mycoplasma* species. In one aspect the bacteria is not *Bacillus anthracis*.

Also disclosed are methods wherein the pathogen is a fungusselected from the group of fungi consisting of *Candida albicans, Cryptococcus neoformans, Histoplama capsulatum, Aspergillus fumigatus, Coccidiodes immitis, Paracoccidioides brasiliensis, Blastomyces dermitidis, Pneumocystis carinii, Penicillium marneffi*, and *Alternaria alternata.*

Also disclosed are methods wherein the pathogen is a parasite selected from the group of parasitic organisms consisting of *Toxoplasma gondii, Plasmodium falciparum, Plasmodium vivax, Plasmodium malariae*, other *Plasmodium* species, *Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium* spp., *Trypanosoma brucei, Trypanosoma cruzi, Leishmania major*, other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis buski, Metagonimus yokogawai, Opisthorchis viverrini, Opisthorchis felineus, Clonorchis sinensis, Trichomonas vaginalis, Acanthamoeba species, Schistosoma intercalatum, Schistosoma haematobium, Schistosoma japonicum, Schistosoma mansoni*, other *Schistosoma* species, *Trichobilharzia regenti, Trichinella spiralis, Trichinella britovi, Trichinella nelsoni, Trichinella nativa*, and *Entamoeba histolytica.*

In one aspect, the methods of treating, inhibiting, reducing, decreasing, ameliorating and/or preventing an autoimmune disease or the symptoms associated with an autoimmune disease or microbial infection are designed to utilize DOR agonists to enhance immunosuppressive microenvironments and thus control the autoimmune disease or symptoms associated with the autoimmune disease or symptoms associated with a microbial infection. It is understood and herein contemplated that any other immunosuppressive agent can be used with the disclosed methods including the use of activators of immune checkpoint proteins such as PD-1, CTLA-4, LAG-3, TIGIT, CD96, BTLA, B7-H3, VISTA, and/or TIM-3.

D. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one *intracellular* pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1 a) Elevated Expression of DOR in Tumor-MDSC Correlates with a Superior Capacity to Impair T Cell Proliferation To determine the correlation of delta opioid receptor (DOR) and Myeloid Derived Suppressor Cells (MDSC) in tumors, subcutaneous B16 tumors were introduced into C57/BL6 mice. The expression of DOR was assessed by flow cytometry in MDSC ($CD45^+CD11b^+Gr1^+$) from the bone marrow (BM), spleen and tumor of C57BL/6 mice bearing s.c. B16 tumors and in $CD45^+CD11b^+Gr1^+$ (iMC) from tumor free controls for 15 days. To follow the proliferation of the cells, CFSE-labelled T cells primed with plate-bound anti-CD3 and anti-CD28 were co-cultured with tumor-MDSC, splenic MDSC, or iMC (1:¼) from B16 bearing mice and sorted. Results showed no significant change in delta opioid expression in the bone marrow or spleen of naïve or tumor bearing mice. However, the tumor showed almost a 50% increase in delta opioid expression in 15 days. Additionally, CFSE staining of T cells showed no significant difference between iMC from naïve mice and spleen MDSC from the spleens of tumor bearing mice with respect to T cell proliferation. However, T cells from tumors showed a significant decrease in proliferation.

b) Tumor-MDSC Display Higher Expression of DOR Compared to Other Tumor-Associated Myeloid Subsets To determine how DOR expression in MDSC compared with other tumor associated myeloid subsets, dendritic cells (DCs), macrophage, and MDSC's from C57BL/6 mice bearing LLC (left), B16 (center), or MC-38 (right) tumors were observed for 15 days. The expression of DOR was detected by flow cytometry. DCs were identified as ($CD45^+$, $CD11b^+$, $Gr1^{neg}$, $F4/80^{neg}$, $CD11c^+$, $MHC\text{-}II^+$), Macrophages were ($CD45^+$, $CD11b^+$, $Gr1^{neg}$, $F4/80^+$, $CD11c^{neg}$, $MHC\text{-}II^{+/neg}$), and MDSC were ($CD45^+$, $CD11b^+$, $Gr1^+$, $F4/80^{neg}$, $CD11c^{neg}$, $MHC\text{-}II^{neg}$). The results show that regardless of the tumor type, the expression of DOR in macrophage and DC were not statistically different. However, DOR expression in MDSC showed at least a 10-fold increase in expression levels.

c) DOR Antagonists Prevent the Development of M-MDSC from Bone Marrow Precursors Next the effect of DOR antagonist on M-MDSC was investigated. Bone marrow precursors were isolated and cultured for 96 hours in GM-CSF and G-CSF (20 ng/ml each) in the presence of increasing concentrations of the DOR antagonists Naltriben mesylate (NTB) or Naltrindole hydrochloride (NTD). Then, we evaluated cell viability by flow cytometry (using DAPI). The results indicate a strong correlation increasing concentration of either NTD or NTB and cell death. The absolute number of generated MDSC ($CD11b^+Gr1^+$) was calculated for increased concentrations of NTD and NTB showing a steady decline of MDSC as concentrations increased. Additionally, the number of M-MDSC ($CD11b^+Ly6G^{neg}Ly6C^{high}$) and PMN-MDSC ($CD11b^+Ly6G^+Ly6C^{low}$) was calculated. While both PMN-MDSC and M-MDSC populations declined in number as the concentration of NTD or NTB increased, the more significant losses were observed in the M-MDSC subset.

d) Materials and Methods (1) Mice

Experiments using mice were developed through an approved Institutional Animal Care and Use Committee (IACUC) protocol (IS00004043) and an active Institutional Biosafety Committee (IBC) study (#1385), both reviewed by the Integrity and Compliance board at the University of South Florida and Moffitt Cancer Center. Thus, the presented work has complied with all the relevant ethical regulations for animal testing and research. Wild type C57BL/6J mice (6 to 8 weeks) were from Envigo (Huntingdon, UK). $Rag1^{KO}$ mice (NOD.129S7 (B6)-$Rag1^{tm1Mom}$/J), $Lyz2^{cre}$ mice (B6.129P2-$Lyz2^{tml(cre)Ifo}$/J) $Tek^{cre}$ mice (B6.Cg-Tg(Tek-cre) 1Ywa/J), $Eif2ak3^{Flox}$ mice (Eif2ak3tm1.2Drc/J), $Nfe2l2^{KO}$ mice (B6.129X1-Nfe2l2tm1Ywk/J), Td-Tomato reporter mice (B6.Cg-Gt(ROSA)$26Sor^{tm9(CAG\text{-}tdTomato)Hze}$/J) and OT-I mice (C57BL/6-Tg (Tcra-Tcrb) 1100Mjb/J) were from the Jackson laboratories (Bar Harbor, ME). $Tmem173^{Flox}$ mice were a kind gift from Dr. John C. Cambier (University of Colorado Denver and National Jewish Health). LSL-K-$Ras^{G12D+}$ $Trp53^{fl/fl}$ mice were developed in (Rutkowski et al., 2015). $Eif2ak3^{KO\text{-}Lyz2}$ mice were created after breeding $Eif2ak3^{Flox}$ mice with $Lyz2^{cre}$ mice; while $Eif2ak3^{KO\text{-}Tek}$ mice were obtained by crossing $Eif2ak3^{Flox}$ and $Tek^{cre}$ mice. Eif2ak3-$Tmem173^{KO\text{-}Lyz2}$ mice were developed after breeding $Eif2ak3^{KO\text{-}Lyz2}$ mice, $Tmem173^{Flox}$ mice, $Lyz2^{cre}$ mice. $Tmem173^{KO}$ mice and were developed after breeding $Tmem173^{Flox}$ and $Lyz2^{Cre}$Lyz2-Td-Tomato and Tek-Td-Tomato reporter mice were developed after crossing $Lyz2^{cre}$ and $Tek^{cre}$ mice with Td-Tomato floxed mice. Mice of the same sex were randomly assigned to all experimental cohorts. All mice were maintained under specific pathogen-free conditions and used at 6-10 weeks of age.

(2) Cell Lines

Lewis lung carcinoma (LLC; #CRL-1642), B16-F10 (#CRL-6475), and EG7 (#CRL-2113) were used for s.c. tumor models and obtained from the American Type Culture Collection (ATCC). Ovarian ID8-Defb29/Vegf-a and Pan02-Ova-ZsGreen cells lines were provided by Dr. Jose Conejo-Garcia and Dr. Shari Pilon Thomas, respectively (Perales-Puchalt et al., 2017; Svoronos et al., 2017). HEK293T cells (#CRL-11268) were obtained from ATCC. All cell lines were validated to be mycoplasma-free using the Universal Mycoplasma Detection Kit (#30-1012K, ATCC), and cultured in RPMI-1640 supplemented with 2 mM L-glutamine, 10 mM HEPES, 150 U/ml streptomycin, 200 U/ml Penicillin, 20 μM β-mercaptoethanol and 10% heat-inactivated Fetal bovine serum (FBS), and maintained at 37° C. in a humidified incubator with 5% $CO_2$.

(3) Tumor Models

Mice were subcutaneously (s.c.) injected with LLC, B16-F10, EG7 or Pan02-Ova-ZsGreen and tumor volume assessed using calipers and calculated using the formula $[(\text{small diameter})^2 \times (\text{large diameter}) \times 0.5]$. For the ovarian carcinoma model; ID8-Defb29/Vegf-a cells were injected intraperitoneal (i.p.) and body weight was assessed daily and mice euthanized when they gained 30% of their body weight. To develop soft tissue autochthonous flank sarcomas, mice with latent mutations in LSL-K-$Ras^{G12D+}$ $Trp53^{fl/fl}$ mice were irradiated for two consecutive days with 550 rads, followed by reconstitution with bone marrow from $Eif2ak3^{Flox}$ or $Eif2ak3^{KO\text{-}Lyz2}$ mice. Autochthonous flank sarcomas were then initiated six weeks later by intramuscular delivery of $2.5 \times 10^8$ plaque-forming units of adenovirus coding for Cre recombinase (Gene Transfer Vector Core, University of Iowa) (Rutkowski et al., 2015). PERK inhibitors AMG-44 (12 or 24 mg/kg), GSK-2606414 (25 mg/kg) were administered i.p. daily and starting at day 6 post-tumor implantation and until study endpoint. Furthermore, mice received i.p. TUDCA (250 mg/kg) or Thapsigargin (Thaps, 100 μg/kg) after tumors were established (day 6 post-LLC injection). To deplete $CD8^+$ T cells, tumor-bearing mice were injected i.p. with 400 μg α-CD8 antibody (clone 53-6.7, BioXcell) at day 0 followed by every 3rd day treatments until experimental endpoint. Same approach was applied for elimination of $Gr1^+$ cells using α-Gr1 antibody (250 μg/mouse, clone RB6-8C5, BioXcell), prevention of myeloid cells mobilization using α-CCL2 (250 μg/mouse, clone 2H5, BioXcell), blockade of PD-L1 (250 μg/mouse, clone 10F.9G2, BioXcell), and neutralization of interferon type 1 receptor using α-IFNAR1 (1 mg/mouse, clone MAR1-5A3, BioXcell). For NRF2 signaling induction, tumor-bearing mice were treated i.p. with D, L-Sulphoraphane (25 mg/kg, 3 days per week) starting at day 6 post-tumor injection.

(4) Flow Cytometry Staining

The conjugated antibodies and probes used for flow cytometry are listed in the Key Resources Table. For surface staining, cells were labelled with the appropriate antibodies in the presence of Fc blocker. For intracellular staining, surface-labeled cells were fixed with Cytofix/Cytoperm™ Solution (BD Biosciences), washed in Perm/Wash™ 1× solution, and labelled with intracellular antibodies. Cells were then washed in Perm/Wash™ 1× and PBS. Live vs. dead cell discrimination was performed prior to antibody labeling by Zombie Fixable Viability dye (Biolegend). Ex vivo intracellular staining for IL-12 and TNFα was performed on isolated cells after stimulation for 6 hours with LPS (1 μg/ml, Sigma Aldrich) in the presence of Golgi stop (0.8 μl/ml, BD Biosciences). For IFNγ staining, cells were incubated for 5 hours with phorbol myristate acetate (PMA, 750 ng/mL, Sigma Aldrich) and ionomycin (50 μg/mL, Sigma-Aldrich) in the presence and Golgi stop (0.8 μl/ml). For ER-tracker and Mitotracker staining, cells were probed with 100 nM of ER tracker green or 200 nM of Mitotracker green (Invitrogen) and then stained for surface markers. For Mitochondrial membrane potential, cells were stained with JC-1 flow cytometry assay kit (Cayman chemicals) followed by surface markers staining. ROS were detected by DCFDA (10 μM) or Dihydroethidium (DHE, 10 μM). Data acquisition was performed in a CytoFLEX II (Beckman Coulter) or LSRII (BD Biosciences). All analysis was performed using FlowJo version 11 software.

(5) Immunofluorescence

Formalin fixed paraffin embedded TMA sections were stained using an automated OPAL-IHC system (PerkinElmer) in a BOND RX (Leica Biosystems). Briefly, slides were treated with the PerkinElmer blocking buffer for 10 min and incubated with the specific primary antibodies, followed by OPAL-HRP polymer and one OPAL fluorophore. Individual antibody complexes were stripped after each round of detection and DAPI applied as the last staining. Auto-fluorescence slides (negative control) included primary and secondary antibodies, omitting the OPAL fluorophores. Slides were imaged with a Vectra®3 Automated Quantitative Pathology Imaging System. Multilayer TIFF images were exported from InForm (PerkinElmer) into HALO (Indica Labs) for quantitative image analysis. Each fluorophore was assigned to a dye color and positivity thresholds determined visually per marker based on nuclear or cytoplasmic staining patterns, and by intensity thresholds normalized for exposure (counts/2 bit depth× exposure time×gain×binning area). Cell segmentation results from each core were analyzed using FCS Express 6 Image Cytometry (De Novo software).

Hematoxylin and Eosin (HE) stained slides were scanned in an Aperio AT2 whole slide scanner (Leica Biosystems Inc.) equipped with a 20×0.7NA objective lens. Images were created at 0.5 micron per pixel resolution and imported into Definiens Tissue Studio software v4.7 (Definiens AG) for analysis. Islets were found using a semi-automated segmentation process. First an automatic segmentation was applied to the image to create contour lines around objects within the image. Objects that contained islets were classified as such and remaining objects were classified as non-islet tissue. Next, adjacent objects of the same classification were merged together to clean up the segmentation. Segmented images were analyzed to provide the total area of islets. Immunofluorescence for mouse insulin in pancreas tissue sections was performed as we described (Sultan et al., 2017). Labeled samples were scanned with a Zeiss Imager Z2 Upright FL microscope with a 10× objective lens using the tile scan function. Images were created at a 0.65 micron per pixel resolution and imported into the Definiens Tissue Studio software v4.7 (Definiens AG) for islet detection and analysis. Islets were detected using a semi-automated segmentation process. First, an automatic segmentation was applied to the image to detect the tissue. Then, the software was trained to detect islet vs. non-islet tissue within the image. In order to remove false detected islets caused by background staining, detected islets larger than 150,000 square microns and less than 600 square microns were reclassified to non-islet tissue. Segmented images were then analyzed to provide the fluorescent intensity of islets and total tissue area.

What is claimed is:

1. A method of mediating an immunosuppressive myelopoiesis in a subject in need thereof comprising administering to the subject a delta opioid receptor (DOR) antagonist, wherein the subject has a cancer associated with DOR expressing myeloid-derived suppressor cells (MDSC), wherein the immunosuppressive myelopoiesis is mediated through the MDSC associated with the cancer of the subject, and wherein the DOR antagonist is selected from 2',6'-dimethyl-L-tyrosyl-1,2,3,4-tetrahydroisoquinoline-3-carboxylic acid (Dmt-Tic-OH), DMT-Tic-Ala-OH, trazodone, nitroindole, natriben, buprenorphine, ICI 174,864 (N,N-diallyl-Tyr-Aib-Aib-Phe-Leu), N-Benzylnaltrindole, BNTX (7-Benzylidenenaltrexone), SoRI-9409, ICI 154,129 (N,N-Diallyl-Tyr-Gly-φ-(CH2S)-Phe-Leu-OH, (+/−)-4-(alpha-R*)-alpha-((2S*,5R*)-4-Allyl-2,5-dimethyl-1-piperazinyl)-3-hydroxybenzyl)-N,N-diethylbenzamide, or SDM25N (4bS,8R,8aS,14bR)-5,6,7,8,14,14b-Hexahydro-7-(2-methyl-2-propenyl)-4,8-methanobenzofuro[2,3-a]pyrido[4,3-b]carbazole-1,8a(9H)-diol, naltrindole hydrochloride, or naltriben mesylate.

2. The method of claim 1, wherein the DOR antagonist is Dmt-Tic-OH, naltriben mesylate (NTB) or naltrindole hydrochloride (NTD).

3. A method of treating, inhibiting, reducing, ameliorating, and/or preventing a cancer and/or metastasis, in a subject comprising administering a combination therapy to a subject;

wherein:

the combination immunotherapy comprises:

an adoptive immunotherapy and a delta opioid receptor (DOR) antagonist; or a delta opioid receptor (DOR) antagonist and an immune system activator;

wherein:

the DOR antagonist is selected from 2',6'-dimethyl-L-tyrosyl-1,23,4-tetrahydroisoquinoline-3-carboxylic acid (Dmt-Tic-OH), DMT-Tic-Ala-OH, trazodone, naltrindole, natriben, buprenorphine, ICI 174,864, (N,N-diallyl-Tyr-Aib-Aib-Phe-Leu), N-Benzylnaltrindole, BNTX (7-Benzylidenenaltrexone), SoRI-9409, ICI 154,129 (N,N-Dialyl-Tyr-Gly-φ-(CH2S)-Phe-Leu-OH, (+/−)-4-((alpha-R*)-alpha-((2S*,5R*)-4-Allyl-2,5-dimethyl-1-piperazinyl)-3-hydroxybenzyl)-N,N-diethylbenzamide, or SDM25N (4bS,8R,8aS,14bR)-5,6,7,8,14,14b-Hexahydro-7-(2-methyl-2-propenyl)-4,8-methanobenzofuro[2,3-alpyrido[4,3-bjcarbazole-1,8a (9H)-diol, naltrindo hydrochloride, or naltriben mesylate.

4. The method of claim 3, wherein the cells of the adoptive immunotherapy are contacted with the DOR antagonist ex vivo prior to administration to the subject.

5. The method of claim 3, wherein the cells of the adoptive immunotherapy are contacted with the DOR antagonist in vivo.

* * * * *